(12) United States Patent
Simonnet et al.

(10) Patent No.: US 7,858,104 B2
(45) Date of Patent: *Dec. 28, 2010

(54) WATER-IN-OIL EMULSION FOUNDATION

(75) Inventors: Jean-Thierry Simonnet, Paris (FR); Aurore Verloo, Bievres (FR); Emmanuelle Ozee, Thiais (FR)

(73) Assignee: L'Oreal S.A., Paris (FR)

( * ) Notice: Subject to any disclaimer, the term of this patent is extended or adjusted under 35 U.S.C. 154(b) by 669 days.

This patent is subject to a terminal disclaimer.

(21) Appl. No.: 10/426,630

(22) Filed: May 1, 2003

(65) Prior Publication Data

US 2004/0009131 A1  Jan. 15, 2004
US 2005/0031560 A9  Feb. 10, 2005

Related U.S. Application Data

(60) Provisional application No. 60/393,115, filed on Jul. 3, 2002.

(30) Foreign Application Priority Data

May 2, 2002  (FR)  .................... 02 05512

(51) Int. Cl.
*A61K 8/02* (2006.01)
*A61K 9/00* (2006.01)

(52) U.S. Cl. ...................... 424/400; 424/401
(58) Field of Classification Search ................ 424/401, 424/63, 78.02, 78.03, 400; 514/63
See application file for complete search history.

(56) References Cited

U.S. PATENT DOCUMENTS

| 5,879,668 | A | * | 3/1999 | Hanna et al. | ............... 424/70.7 |
|---|---|---|---|---|---|
| 5,942,213 | A | * | 8/1999 | Bara et al. | ..................... 424/63 |
| 5,976,510 | A | * | 11/1999 | Cernasov et al. | ............... 424/59 |
| 6,638,519 | B1 | * | 10/2003 | Lorant | ........................ 424/401 |
| 2003/0228339 | A1 | * | 12/2003 | El-Nokaly et al. | .......... 424/401 |
| 2005/0008592 | A1 | * | 1/2005 | Gardel et al. | ................. 424/63 |

FOREIGN PATENT DOCUMENTS

| EP | 1 086 687 | 3/2001 |
|---|---|---|
| EP | 1 097 703 | 5/2001 |
| FR | 2 686 510 | 7/1993 |
| FR | 2 776 183 | 9/1999 |

OTHER PUBLICATIONS

English language abstract of EP 1 086 687, Mar. 28, 2001.
English language abstract of EP 1 097 703, May 9, 2001.
English language abstract of FR 2 776 183, Sep. 24, 1999.
Leon M. Prince Ed, "Microemulsions Theory and Practice," Academic Press, 1977, pp. 21-32.

* cited by examiner

*Primary Examiner*—Johann R Richter
*Assistant Examiner*—Kristie L Brooks
(74) *Attorney, Agent, or Firm*—Finnegan, Henderson, Farabow, Garrett & Dunner LLP

(57) ABSTRACT

A foundation composition in the form of a water-in-oil emulsion comprising a fatty phase; an aqueous phase; at least one silicone surfacant chosen from $C_8$-$C_{22}$ alkyl dimethicone copolyols; and at least 5% by weight, relative to the total weight of the composition, of hydrophobic coated pigments; provided that the composition is free of polyglyceryl-4 isostearate or comprises polyglyceryl-4 isostearate in a quantity such that the weight ratio of the $C_8$-$C_{22}$ alkyl dimethicone copolyol to the polyglyceryl-4 isostearate is greater than or equal to 2:1, wherein the foundation composition can exhibit good stability at room temperature and can be easy to apply to the skin.

40 Claims, No Drawings

WATER-IN-OIL EMULSION FOUNDATION

This application claims benefit of U.S. Provisional Application No. 60/393,115, filed Jul. 3, 2002.

Disclosed herein is a fluid foundation cosmetic composition in the form of a water-in-oil emulsion comprising at least one silicone surfactant and coated pigments. Also disclosed herein is a method for applying make-up to skin comprising applying the foundation to the skin.

The foundation composition disclosed herein is a make-up composition for the skin of human beings. The compositions disclosed herein may, for example, be provided in at least one of the following forms: foundations to be applied to the face or the neck; a concealer; a tinted cream; and a make-up composition for the body.

Foundation compositions are commonly used to give an aesthetic colour to the skin, for example, to the face, but also can be used to conceal skin imperfections, such as redness and spots.

It is known from the document FR-A-2686510 that fluid emulsions of water-in-oil foundations comprise, as a surfactant, ABIL® WE 09 sold by the company Goldschmidt, which is a mixture of cetyl dimethicone copolyol, polyglyceryl-4 isostearate and hexyl laurate in a 40/30/30 weight ratio. However, it has been observed that the fluid emulsions prepared with this mixture may not be stable over time: the emulsion, after storing for 4 months at room temperature (25° C.), can release oil at the surface of the composition and, therefore, may no longer be homogeneous. Without prior stirring, the application of such a composition to the skin may leave a sensation of greasiness which can damage at least one of the qualities sought for the foundation, for example, ease of application to the skin, pleasant feel and drying speed. The resistance of the mattness of the make-up can be impaired, and as a result, the make-up can rapidly appear glossy. Therefore, the make-up thus obtained may not be aesthetic.

The embodiments disclosed herein may, for example, provide a foundation composition which can have good stability after storing at room temperature (25° C.) for at least 4 months and which may make it possible to obtain a homogeneous make-up on the skin, which may have at least one satisfactory aesthetic quality.

The inventors have discovered that such a foundation composition could be obtained using hydrophobic coated pigments and at least one silicone surfactant chosen from alkyl dimethicone copolyols and polyglyceryl-4 isostearates in particular quantities or even after removing the polyglyceryl-4 isostearates from the composition.

For example, disclosed herein is a foundation composition in the form of a water-in-oil emulsion comprising a fatty phase; an aqueous phase; at least one silcone surfactant chosen from $C_8$-$C_{22}$ alkyl dimethicone copolyols; and at least 5% by weight, relative to the total weight of the composition, of hydrophobic coated pigments; provided that the composition is free of polyglyceryl-4 isostearate or comprises polyglyceryl-4 isostearate in a quantity such that the weight ratio of the $C_8$-$C_{22}$ alkyl dimethicone copolyol to the polyglyceryl-4 isostearate is greater than or equal to 2:1.

Further disclosed herein is a cosmetic method for non-therapeutic application of make-up to the skin, which comprises applying to the skin the composition defined above.

Also disclosed herein is the use of the at least one silicone surfactant chosen from $C_8$-$C_{22}$ alkyl dimethicone copolyols in a foundation composition in the form of a water-in-oil emulsion comprising at least 5% by weight, relative to the total weight of the composition, of hydrophobic coated pigments; provided that the composition is free of polyglyceryl-4 isostearate or comprises polyglyceryl-4 isostearate in a quantity such that the weight ratio of the $C_8$-$C_{22}$ alkyl dimethicone copolyol to the polyglyceryl-4 isostearate is greater than or equal to 2:1; in order to obtain a foundation composition which can have at least one of the following qualities: stability, homogeneity, and easy application to the skin, and a homogeneous application of make-up to the skin.

The foundation compositions disclosed herein may have very good stability at room temperature (25° C.), for example, after storage for 4 months, further, for example, after 6 months, and even further, for example, after 8 months. The foundation compositions disclosed herein can also have at least one quality of being easily applied to the skin, with a sensation of unctuousness, softness and non-greasiness, rapid drying, and spreading homogeneously on the skin. The make-up obtained may also exhibit good stability of the mattness over time.

The $C_8$-$C_{22}$ alkyl dimethicone copolyols present in the foundation compositions disclosed herein may, for example, be chosen from at least one of oxypropylenated and oxyethylenated polymethyl ($C_8$-$C_{22}$) alkyl dimethyl methyl siloxanes.

The $C_8$-$C_{22}$ alkyl dimethicone copolyols may, for example, be chosen from compounds of the following formula (I):

$$(CH_3)_3Si-O-\left[\begin{array}{c}CH_3\\|\\Si-O\\|\\(CH_2)_p\\|\\CH_3\end{array}\right]_o\left[\begin{array}{c}CH_3\\|\\Si-O\\|\\(CH_2)_q\\|\\O\\|\\PE\end{array}\right]_m\left[\begin{array}{c}CH_3\\|\\Si-O\\|\\CH_3\end{array}\right]_n-Si(CH_3)_3$$

wherein:
PE is chosen from groups of $(-C_2H_4O)_x-(C_3H_6O)_y-R$,
  wherein
    R is chosen from a hydrogen atom and alkyl radicals comprising from 1 to 4 carbon atoms,
    x ranges from 0 to 100, and
    y ranges from 0 to 80, provided that the x and the y are not simultaneously 0;
m ranges from 1 to 40;
n ranges from 10 to 200;
o ranges from 1 to 100;
p ranges from 7 to 21; and
q ranges from 0 to 4;

and, for example:
R=H;
m=1 to 10;
n=10 to 100;
o=1 to 30;
p=15; and
q=3.

For example, the $C_8$-$C_{22}$ alkyl dimethicone copolyols may be chosen from cetyl dimethicone copolyols such as the product marketed under the name Abil® EM 90 by the company Goldschmidt.

The $C_8$-$C_{22}$ alkyl dimethicone copolyols may be present, for example, in the compositions disclosed herein in an amount ranging from 2% to 10% by weight, relative to the total weight of the composition, and further, for example, ranging from 2.5% to 5% by weight, relative to the total weight of the composition.

The polyglyceryl-4 isostearate may comprise 4 ethylene oxide units. It may be absent from the compositions disclosed herein or may be present in an amount such that the weight ratio of the $C_8$-$C_{22}$ alkyl dimethicone copolyol to the polyglyceryl-4 isostearate is, for example, greater than or equal to 2:1 and, further, for example, greater than or equal to 3:1.

The hydrophobic coated pigments present in the compositions disclosed herein are pigments which can be surface-treated with at least one hydrophobic agent in order to make them compatible with the fatty phase of the emulsion, for example, for them to have good wettability with the oils of the fatty phase. Thus, these treated pigments may be well dispersed in the fatty phase.

The pigments intended to be coated may be chosen from at least one of inorganic and organic pigments. The pigments may, for example, be chosen from at least one of metal oxides such as iron oxides, for example, those which are yellow, red, brown and black in colour, titanium dioxides, cerium oxide, zirconium oxide, chromium oxide; manganese violet, ultramarine blue, Prussian blue, ferric blue, bismuth oxychloride, pearl, mica coated with at least one of titanium dioxide and bismuth oxychloride, coloured pearlescent pigments such as mica-titanium with iron oxides, mica-titanium with, for example, ferric blue and chromium oxide, mica-titanium with an organic pigment of the abovementioned type and pearlescent pigments based on bismuth oxychlorides.

For example, pigments chosen from iron oxides and titanium dioxide may be used in the compositions disclosed herein.

The at least one hydrophobic treatment agent may be chosen, for example, from silicones such as methicones, dimethicones, and perfluoroalkylsilanes; fatty acids such as stearic acid; metal soaps such as aluminium dimyristate and aluminium salt of hydrogenated tallow glutamate; perfluoroalkyl phosphates; perfluoroalkylsilanes; perfluoroalkylsilazanes; polyhexafluoropropylene oxides; polyorganosiloxanes comprising at least one perfluoroalkyl perfluoropolyether group; amino acids; N-acylated amino acids and the salts thereof; lecithin; and isopropyl triisostearyl titanate.

The N-acylated amino acids may comprise, for example, at least one acyl group comprising from 8 to 22 carbon atoms, such as 2-ethylhexanoyl, caproyl, lauroyl, myristoyl, palmitoyl, stearoyl and cocoyl groups. The salts of these compounds may be chosen from aluminium, magnesium, calcium, zirconium, zinc, sodium and potassium salts. The amino acid may be, for example, chosen from lysine, glutamic acid and alanine.

The term "alkyl" as used herein means an alkyl group comprising from 1 to 30 carbon atoms, for example, comprising from 5 to 16 carbon atoms.

Hydrophobic treated pigments are, for example, described in Patent Application No. EP-A-1086683.

The hydrophobic coated pigments may be present in an amount ranging, for example, from 5% to 20% by weight, relative to the total weight of the composition, further, for example, in an amount at least equal to 8% by weight, and even further, for example, in an amount ranging from 8% to 15% by weight, relative to the total weight of the composition.

The fatty phase of the compositions disclosed herein may, for example, further comprise at least one oil.

The compositions disclosed herein may, for example, comprise from 20% to 45% by weight of oil, relative to the total weight of the composition, and further, for example, from 20% to 42% by weight of oil, and even further, for example, from 30% to 38% by weight of oil, relative to the total weight of the composition.

The compositions disclosed herein, may comprise at least one oil chosen from silicone oils, for example, volatile silicone oils.

The at least one oil may be chosen, for example, from carbonaceous and hydrocarbonaceous oils and silicone oils of mineral, animal, vegetable and synthetic origins.

For example, the hydrocarbonaceous oils may be chosen from paraffin oils, liquid paraffin oils, vison oil, turtle oil, soya bean oil, perhydrosqualene, sweet almond oil, calophyllum oil, palm oil, grapeseed oil, sesame oil, maize oil, arara oil, rapeseed oil, sunflower oil, cottonseed oil, apricot oil, castor oil, avocado oil, jojoba oil, olive oil and cereal germ oil; esters of lanolic acid, oleic acid, lauric acid and stearic acid; fatty esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyidodecyl myristate, 2-octyldodecyl lactate, 2-diethylhexyl succinate, diisostearyl malate, glycerine triisostearate, diglycerine triisostearate; higher fatty acids such as myristic acid, palmitic acid, stearic acid, behenic acid, oleic acid, linoleic acid, linolenic acid, and isostearic acid; higher fatty alcohols such as cetanol, stearyl alcohol, oleyl alcohol, linoleyl alcohol, linolenyl alcohol, isostearyl alcohol, and octyldodecanol.

The silicone oils may, for example, be chosen from at least one of polysiloxanes modified with at least one entity chosen from fatty acids, fatty alcohols and polyoxyalkylenes; polydimethylsiloxane (PDMS), which may be optionally phenylated, such as phenyltrimethicones, and which may be optionally substituted with at least one group chosen from aliphatic groups, aromatic groups, and functional groups such as hydroxyl, thiol and amine groups.

For example, it is possible to use at least one oil which is volatile at room temperature. The expression "volatile oils" means oils which are capable of evaporating from the skin, at room temperature in less than one hour. For example, volatile oils can have a viscosity ranging from 0.5 to 25 centistokes at 25° C. Such a viscosity can readily be determined by one of ordinary skill in the art using the known techniques.

The volatile oils may be chosen, for example, from hydrocarbonaceous oils and silicone oils optionally comprising at least one group chosen from alkyl and alkoxy groups at the end of a silicone and/or pendant chain. The volatile oils may, for example, be chosen from volatile silicone oils.

The volatile silicone oils, which can be used in the compositions disclosed herein, may, for example, be chosen from linear and cyclic silicones comprising from 2 to 7 silicon atoms, these silicones optionally comprising at least one group chosen from alkyl and alkoxy groups comprising from 1 to 10 carbon atoms. For example, the volatile silicone oils may be chosen from at least one of octamethylcyclotetrasiloxane, decamethylcyclopentasiloxane, hexadecamethyl-cyclohexasiloxane, heptamethylhexyltrisiloxane, and heptamethyloctyltrisiloxane.

The volatile hydrocarbonaceous oils may be chosen, for example, from at least one of $C_8$-$C_{16}$ isoparaffins such as isooctane, isododecane, isodecane, isohexadecane, and heptane.

These volatile oils may be present in the compositions disclosed herein in an amount ranging, for example, from 20% to 45% by weight, and further, for example, from 25% to 40% by weight, and even further, for example, from 30 to 40% by weight, relative to the total weight of the composition.

The fatty phase may also comprise at least one fatty substance chosen, for example, from waxes, gums, and pasty fatty substances, which may be chosen from pasty fatty substances of vegetable origin, animal origin, mineral origin, synthetic origin, and silicone-based fatty substances.

Among the waxes solid at room temperature, which may be present in the compositions disclosed herein, these waxes may be chosen, for example, from hydrocarbon waxes such as beeswax, Carnauba wax, Candelilla wax, Ouricoury wax, Japan wax, cork fibre waxes, sugarcane waxes, paraffin waxes, lignite waxes, microcrystalline waxes, lanolin wax, Montan wax, ozokerites, polyethylene waxes, waxes obtained by Fischer-Tropsch synthesis, hydrogenated oils, fatty esters and glycerides which are concrete at 25° C. It may also be possible to use waxes chosen, for example, from silicone waxes, such as alkyl, alkoxy and esters of polymethylsiloxane. The waxes may be provided in the form of stable dispersions of colloidal particles of wax as may be prepared according to known methods, such as those of "Microemulsions Theory and Practice", L. M. Prince Ed., Academic Press (1977), pages 21-32.

A wax which is liquid at room temperature, such as jojoba oil, may also be used in the compositions disclosed herein.

The waxes may be present in an amount ranging, for example, from 0.1% to 10% by weight, relative to the total weight of the composition.

The pasty fatty compounds may be defined by at least one of the following physicochemical properties:

a viscosity ranging from 0.1 to 40 Pa.s (1 to 400 poises), for example, ranging from 0.5 to 25 Pa.s, measured at 40° C. with a CONTRAVES TV rotary viscometer equipped with an MS-r3 or MS-r4 rotor at a frequency of 60 Hz, and a melting point ranging from 25 to 70° C., for example, ranging from 25 to 55° C.

The compositions disclosed herein may also comprise at least one component chosen from alkyl, alkoxy and phenyl dimethicone such as the product sold under the name "Abil wax 2440" by the company GOLDSCHMIDT.

The compositions disclosed herein may also comprise at least one silicone resin comprising a combination of $(R)_3SiO_{1/2}$, $(R)_2SiO_{2/2}$, $RSiO_{3/2}$ and $SiO_{4/2}$ units wherein R is chosen from alkyl radicals comprising from 1 to 6 carbon atoms.

The compositions disclosed herein may further comprise at least one fatty phase thickening agent. The at least one fatty phase thickening agent may be chosen from:

organomodified clays which are clays treated with compounds chosen, for example, from quaternary amines and tertiary amines. The organomodified clays may, for example, be chosen from organomodified bentonites such as those sold under the name "Bentone 34" by the company RHEOX, and organomodified hectorites such as those sold under the name "Bentone 27", "Bentone 38" by the company RHEOX; and hydrophobic pyrogenic silicas, which are pyrogenic silicas that are chemically surface-modified by a chemical reaction generating a reduction in the number of silanol groups. The silanol groups may be replaced, for example, by at least one hydrophobic group.

The at least one hydrophobic group may, for example, be chosen from:

trimethylsiloxyl groups, which are obtained, for example, by treating pyrogenic silicas in the presence of hexamethyldisilazane. Silicas thus treated are called "Silica silylate" according to CTFA ($6^{th}$ edition, 1995). They are, for example, marketed under the references "AEROSIL R812®" by the company Degussa, and "CAB-O-SIL TS-530®" by the company Cabot.

dimethylsilyloxyl and polydimethylsiloxane groups, which are, for example, obtained by treating pyrogenic silicas in the presence of polydimethylsiloxane or dimethyldichlorosilane. Silicas thus treated are called "Silica dimethyl silylate" according to CTFA ($6^{th}$ edition, 1995). They are, for example, marketed under the references "AEROSIL R972®", and "AEROSIL R974®" by the company Degussa, and "CAB-O-SIL TS-610®", and "CAB-O-SIL TS-720®" by the company Cabot.

The pyrogenic silicas may have, for example, an average particle size, which may be nanometric or micrometric, for example, ranging from 5 to 200 nm. Such an average particle size can readily be determined by one of ordinary skill in the art using the known techniques.

The at least one fatty phase thickening agent may be present in an amount ranging, for example, from 0.1% to 5% by weight, relative to the total weight of the composition, and further, for example, from 0.4% to 3% by weight, relative to the total weight of the composition.

The fatty phase, comprising at least one silicone surfactant chosen from $C_8$-$C_{22}$ alkyl dimethicone copolyols and optionally polyglyceryl-4 isostearates if present, may be present in an amount ranging, for example, from 22% to 50% by weight, relative to the total weight of the composition, further, for example, from 25% to 45% by weight, and even further, for example, from 30% to 40% by weight, relative to the total weight of the composition.

The aqueous phase comprises water. The water may be chosen from at least one of floral water such as cornflower water; mineral water such as VITTEL water, LUCAS water and LA ROCHE POSAY water; and thermal water.

The aqueous phase may also comprise at least one solvent other than water. For example, the at least one solvent may be chosen from primary alcohols such as ethanol and isopropanol; glycols such as propylene glycol, butylene glycol, dipropylene glycol, and diethylene glycol; and glycol ethers such as $(C_1$-$C_4)$alkyl ethers of mono-, di- and tripropylene glycols, and mono-, di- and triethylene glycols.

The aqueous phase may further comprise at least one stabilizing agent. The at least one stabalizing agent may be chosen, for example, from sodium chloride, magnesium dichloride and magnesium sulphate.

The aqueous phase may also comprise at least one entity chosen from water-soluble and water-dispersible entities compatible with an aqueous phase, such as gelling agents, film-forming polymers, thickeners, and surfactants.

For example, the aqueous phase may be present in the compositions disclosed herein in an amount ranging from 30% to 75% by weight, further, for example, from 35% to 50% by weight, relative to the total weight of the composition.

The compositions disclosed herein may further comprise at least one filler. The expression "filler" means colourless or white, inorganic or synthetic, lamellar or nonlamellar particles.

The at least one filler may be present in the compositions disclosed herein in an amount ranging, for example, from 0.1% to 15% by weight, relative to the total weight of the composition, further, for example, from 0.1% to 10% by weight, relative to the total weight of the composition. The at least one filler may be chosen, for example, from talc, mica, silica, kaolin, starch, boron nitride, calcium carbonate, magnesium carbonate, magnesium hydrocarbonate, microcrystalline cellulose, powders of synthetic polymers such as polyethylene, polyesters, polyamides such as those sold under the tradename "Nylon", and polytetrafluoroethylene ("Teflon") and silicone powders.

For example, the compositions disclosed herein may be fluid (flows under its own weight at room temperature) and may have a viscosity, measured at 25° C., at a shear rate of 200 min$^{-1}$ (200 revolutions per minute, that is a frequency of 50 Hz), ranging, for example, from 0.5 to 3.2 Pa.s (5 to 32 poises), and further, for example, ranging from 0.6 to 1.5 Pa.s (6 to 15 poises). Such a viscosity may allow easy application of the composition, and may make it possible to obtain a make-up which is homogeneous, uniform and without traces. The viscosity is measured at 25° C. with a TV type CONTRAVES viscometer equipped with a No. 3 rotor, the measurement being carried out after 10 minutes of rotation of the rotor (time after which stabilization of the viscosity and of the speed of rotation of the rotor is observed), at a shear rate of 200 min$^{-1}$ (200 revolutions per minute).

The compositions disclosed herein may comprise, for example, at least one adjuvant chosen from customary adjuvants used in the cosmetic and dermatological fields, such as hydrophilic and lipophilic gelling and thickening agents; moisturizing agents; emollients; hydrophilic and lipophilic active agents; anti-free radical agents; sequestrants; antioxidants; preservatives; basifying and acidifying agents; perfumes; film-forming agents; and soluble colorants. The quantity of the at least one adjuvant is that conventionally used in the fields considered.

Active agents, which can be used in the compositions disclosed herein, may be chosen, for example, from at least one of moisturizing agents such as protein hydrolysates and polyols such as glycerine, glycols such as polyethylene glycols, and sugar derivatives; natural extracts; anti-inflammatory agents; procyannidolic oligomers; vitamins such as vitamin A (retinol), vitamin E (tocopherol), vitamin C (ascorbic acid), vitamin B5 (panthenol), vitamin B3 (niacinamide), and derivatives thereof, for example, esters; urea, caffeine, salicylic acid and its derivatives; alpha-hydroxy acids such as lactic acid and glycolic acid and derivatives thereof; retinoids such as carotenoids and derivatives of vitamin A; sunscreens; hydrocortisone; melatonin; extracts of algae, fungi, plants, yeasts and bacteria; enzymes; steroids; anti-bacterial active agents such as 2,4,4'-trichloro-2'-hydroxydiphenyl ether (or triclosan), 3,4,4'-trichlorocarbanilide (or triclocarban) and the acids indicated above, for example, salicylic acid and its derivatives; and tightening agents.

The sunscreens (or UV-screening agents) may be chosen from at least one of organic (or chemical) screening agents and physical screening agents.

The organic (or chemical) sunscreens, which may be used in the compositions disclosed herein may be chosen, for example, from any UVA- and UVB-screening agents which may be used in the cosmetic field.

The UVB-screening agents may, for example, be chosen from at least one of:
(1) salicylic acid derivatives, for example, homomenthyl salicylate and octyl salicylate;
(2) cinnamic acid derivatives, for example, 2-ethylhexyl p-methoxycinnamate, marketed by the company Givaudan under the name Parsol MCX;
(3) liquid β,β'-diphenylacrylate derivatives, for example, 2-ethylhexyl α-cyano-α,β'-diphenylacrylate and octocrylene, marketed by the company BASF under the name UVINUL N539;
(4) p-aminobenzoic acid derivatives;
(5) 4-methylbenzylidenecamphor marketed by the company Merck under the name EUSOLEX 6300;
(6) 2-phenylbenzimidazole-5-sulphonic acid marketed under the name EUSOLEX 232 by the company Merck; and
(7) 1,3,5-triazine derivatives, for example:
  2,4,6-tris[p-(2'-ethylhexyl-1'-oxycarbonyl)anilino]-1,3,5-triazine marketed by the company BASF under the name UVINUL T150, and
  dioctylbutamidotriazone marketed by the company Sigma 3V under the name UVASORB HEB.

The UVA-screening agents may be chosen, for example, from at least one of:
(1) dibenzoylmethane derivatives, for example, 4-(tert-butyl)-4'-methoxydibenzoylmethane marketed by the company Givaudan under the name PARSOL 1789;
(2) 1,4-benzene[di(3-methylidene-10-camphorsulphonic)] acid optionally in partially and completely neutralized form, marketed under the name MEXORYL SX by the company Chimex;
(3) benzophenone derivatives, for example:
  2,4-dihydroxybenzophenone (benzophenone-1);
  2,2',4,4'-tetrahydroxybenzophenone (benzophenone-2);
  2-hydroxy-4-methoxybenzophenone (benzophenone-3), marketed under the name UVINUL M40 by the company BASF;
  2-hydroxy-4-methoxybenzophenone-5-sulphonic acid (benzophenone-4) and its sulphonate form (benzophenone-5), marketed by the company BASF under the name UVINUL MS40;
  2,2'-dihydroxy-4,4'-dimethoxybenzophenone (benzophenone-6);
  5-chloro-2-hydroxybenzophenone (benzophenone-7);
  2,2'-dihydroxy-4-methoxybenzophenone (benzophenone-8);
  the disodium salt of 2,2'-dihydroxy-4,4'-dimethoxybenzophenone-5,5'-disulphonic diacid (benzophenone-9);
  2-hydroxy-4-methoxy-4'-methylbenzophenone (benzophenone-10);
  benzophenone-11;
  2-hydroxy-4-(octyloxy)benzophenone (benzophenone-12);
(4) silane derivatives and polyorganosiloxanes comprising at least one benzophenone group;
(5) anthranilates, for example, menthyl anthranilate marketed by the company Haarman & Reimer under the name NEO HELIOPAN MA;
(6) compounds comprising, per molecule, at least two benzoazolyl groups or at least one benzodiazolyl group, for example, 1,4-bis-benzimidazolyl-phenylene-3,3',5,5'-tetrasulphonic acid, and its salts, marketed by the company Haarman & Reimer;
(7) silicon-containing derivatives of N-substituted benzimidazolyl-benzazoles and of benzofuranyl-benzazoles, for example:
  2-[1-[3-[1,3,3,3-tetramethyl-1-[(trimethylsilyl)oxy]disiloxanyl]propyl]-1H-benzimidazol-2-yl]benzoxazole;
  2-[1-[3-[1,3,3,3-tetramethyl-1-[(trimethylsilyl)oxy]disiloxanyl]propyl]-1H-benzimidazol-2-yl]benzothiazole;
  2-[1-(3-trimethylsilanylpropyl)-1H-benzimidazol-2-yl]benzoxazole;
  6-methoxy-1,1'-bis(3-trimethylsilanylpropyl)-1H,1'H-[2,2']dibenzimidazolylbenzoxazole;
  2-[1-(3-trimethylsilanylpropyl)-1H-benzimidazol-2-yl]benzothiazole;

which are described in Patent Application No. EP-A-1 028 120; and (8) triazine derivatives, for example, 2,4-bis{[4-(2-ethylhexyloxy)-2-hydroxy]phenyl}-6-(4-methoxyphenyl)-1,3, 5-triazine marketed by the company Ciba Geigy under the name TINOSORB S, and 2,2'-methylenebis-[6-(2H-benzotriazol-2-yl)-4-(1,1,3,3-tetramethylbutyl)phenol] marketed by the company Ciba Geigy under the name TINOSORB M.

It is also possible to use a mixture of several of these screening agents, e.g., a mixture of UVB-screening agents, and UVA-screening agents, and at least one of the physical screening agents.

The physical screening agents may, for example, be chosen from at least one of titanium oxide (amorphous and crystalline titanium dioxide in rutile and anatase forms), zinc oxide, iron oxide, zirconium oxide, and cerium oxide. These metal oxides may, for example, be in the form of particles having a micrometric or nanometric size (nanopigments). In the form of nanopigments, the average sizes of the particles can range, for example, from 5 to 100 nm. Such an average particle size can readily be determined by one of ordinary skill in the art using the known techniques.

These pigments may, for example, be treated so as to make their surface hydrophobic. The treatment may be carried out according to methods known to persons skilled in the art. The pigments may, for example, be coated with silicone compounds such as PDMS and/or with polymers.

Of course, persons skilled in the art will be careful to choose the possible adjuvant(s) added to the compositions disclosed herein such that the advantageous properties intrinsically attached to the compositions disclosed herein are not, or not substantially, impaired by the addition envisaged.

The embodiments disclosed herein are illustrated in greater detail in the following examples.

EXAMPLE 1

A foundation was prepared in the form of a water-in-oil emulsion having the following composition:

| Fatty phase: | | |
|---|---|---|
| isostearyl palmitate | | 6 g |
| cyclopentasiloxane | | 30 g |
| cetyl dimethicone copolyol | | 2.7 g |
| (Abil ® EM 90 from the company GOLDSCHMIDT) | | |
| polyglyceryl-4 isostearate | | 0.9 g |
| iron oxides coated with disodium salt of stearoyl glutamate | | 2 g |
| titanium oxide coated with disodium salt of stearoyl glutamate | | 9 g |
| nylon powder | | 5 g |
| hectorite | | 0.5 g |
| hydrophobic pyrogenic silica (Aerosil R 972) | | 0.35 g |
| hollow microspheres (Expancel) | | 0.35 g |
| Aqueous phase: | | |
| butylene glycol | | 5 g |
| magnesium sulphate | | 1 g |
| PEG 20 | | 1.7 g |
| preservatives | qs | |
| water | qs | 100 g |

The emulsion was prepared at room temperature, on the one hand, by mixing the pigments in part of the cyclopentasiloxane, on the other hand, by mixing the other oils with the surfactants and dispersing the hectorite therein, and then the mixture of pigments and fillers was added to the other mixed constituents of the fatty phase. The mixture of the constituents of the aqueous phase was then prepared and poured into the mixture of the fatty phase, with stirring, according to known means in order to finally obtain the emulsion.

This foundation was stable after storing at room temperature (25° C.) for 4 months, or even up to 8 months. It was easy to apply to the skin with a good sensation to the touch, dried rapidly after application, and the make-up obtained exhibited good colour homogeneity.

EXAMPLE 2

A foundation was prepared in the form of a water-in-oil emulsion having the following composition:

| Fatty phase: | | |
|---|---|---|
| cyclohexasiloxane | | 33 g |
| cetyl dimethicone copolyol | | 4 g |
| (Abil ® EM 90 from the company GOLDSCHMIDT) | | |
| iron oxides coated with disodium salt of stearoyl glutamate | | 2 g |
| titanium oxide coated with disodium salt of stearoyl glutamate | | 7 g |
| hectorite | | 0.7 g |
| silica (Aerosil R 972) | | 0.6 g |
| Aqueous phase: | | |
| glycerol | | 3 g |
| sodium chloride | | 0.5 g |
| preservatives | qs | |
| water | qs | 100 g |

The emulsion was prepared according to the same procedure described in Example 1.

This foundation was stable after storing at room temperature (25° C.) for 4 months, or even up to 8 months. It was easy to apply to the skin with a good sensation to the touch, dried rapidly during application, and the make-up obtained exhibited good colour homogeneity without leaving traces.

What is claimed is:

1. A foundation composition in the form of a water-in-oil emulsion comprising a fatty phase;

an aqueous phase;

at least one silicone surfactant chosen from $C_8$-$C_{22}$ alkyl dimethicone copolyols;

at least 5% by weight, relative to the total weight of the composition, of hydrophobic coated pigments;

at least one oil;

and a polyglyceryl-4 isostearate in a quantity such that the weight ratio of the $C_8$-$C_{22}$ alkyl dimethicone copolyol to the polyglyceryl-4 isostearate is greater than or equal to 2:1, wherein said at least one oil is chosen from at least one of octamethylcyclotetrasiloxane, decamethylcyclopentasiloxane, hexadecamethyl-cyclohexasiloxane, heptamethylhexyltrisiloxane, heptamethyloctyltrisiloxane., polydimethylsiloxanes, phenylated silicone oils, polysiloxanes modified with at least one entity chosen from fatty acids, fatty alcohols, and polyoxyalkylenes, paraffin oils, liquid paraffin oils, soya bean oil, perhydrosqualene, sweet almond oil, calophyllum oil, palm oil, grapeseed oil, sesame oil, maize oil, arara oil, rapeseed oil, sunflower oil, cottonseed oil, apricot oil, castor oil, avocado oil, jojoba oil, olive oil, cereal germ oil; esters of lanolic acid, oleic acid, lauric acid, stearic acid; isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate, 2-octyldodecyl lactate, 2-diethylhexyl succinate, diisostearyl malate, glycerine triisostearate, diglycerine triisostearate; myristic acid, palmitic acid, stearic acid, behenic acid, oleic acid, linoleic acid, linolenic acid, isostearic acid; cetanol, stearyl alcohol, oleyl alcohol, linoleyl alcohol, linolenyl alcohol, isostearyl alcohol, and octyldodecanol.

2. The foundation composition according to claim 1, wherein the $C_8$-$C_{22}$ alkyl dimethicone copolyols are chosen from compounds of the following formula

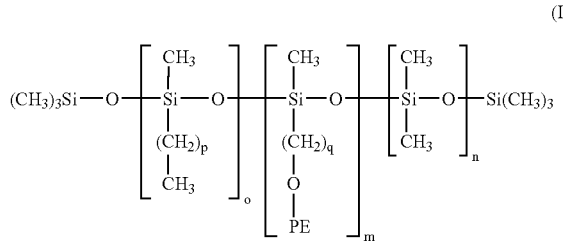

(I)

wherein:
PE is chosen from groups of $(-C_2H_4O)_x-(C_3H_6O)_y$-R, wherein
R is chosen from a hydrogen atom and alkyl radicals comprising from 1 to 4 carbon atoms,
x ranges from 0 to 100, and
y ranges from 0 to 80, provided that the x and the y are not simultaneously 0;
m ranges from 1 to 40;
n ranges from 10 to 200;
o ranges from 1 to 100;
p ranges from 7 to 21; and
q ranges from 0 to 4.

3. The foundation composition according to claim 2, wherein
R =H;
m =1 to 10;
n =10 to 100;
o =1 to 30;
p =15; and
q =3.

4. The foundation composition according to claim 1, wherein the $C_8$-$C_{22}$ alkyl dimethicone copolyols are chosen from cetyl dimethicone copolyols.

5. The foundation composition according to claim 1, wherein the at least one silicone surfactant chosen from $C_8$-$C_{22}$ alkyl dimethicone copolyols is present in an amount ranging from 2% to 10% by weight, relative to the total weight of the composition.

6. The foundation composition according to claim 1, wherein the at least one silicone surfactant chosen from $C_8$-$C_{22}$ alkyl dimethicone copolyols is present in an amount ranging from 2.5% to 5% by weight, relative to the total weight of the composition.

7. The foundation composition according to claim 1, wherein the polyglyceryl-4isostearate is present in an amount such that the weight ratio of the $C_8$-$C_{22}$ alkyl dimethicone copolyol to the polyglyceryl-4isostearate is greater than or equal to 3:1.

8. The foundation composition according to claim 1, wherein the hydrophobic coated pigments are chosen from pigments treated with at least one hydrophobic agent.

9. The foundation composition according to claim 8, wherein the pigments are chosen from at least one of metal oxides, manganese violet, ultramarine blue, Prussian blue, ferric blue, bismuth oxychloride, pearl, mica coated with titanium dioxide, mica coated with bismuth oxychloride, and coloured pearlescent pigments.

10. The foundation composition according to claim 9, wherein the pigments are chosen from at least one of iron oxides and titanium dioxides.

11. The foundation composition according to claim 8, wherein the at least one hydrophobic agent is chosen from silicones, fatty acids, metal soaps, perfluoroalkyl phosphates, perfluoroalkylsilanes, perfluoroalkylsilazanes, polyhexafluoropropylene oxides, polyorganosiloxanes comprising at least one perfluoroalkyl perfluoropolyether group, amino acids, N-acylated amino acids and salts thereof, lecithin, and isopropyl triisostearyl titanate.

12. The foundation composition according to claim 11, wherein the N-acylated amino acids comprise at least one acyl group comprising from 8 to 22 carbon atoms.

13. The foundation composition according to claim 1, wherein the hydrophobic coated pigments are present in an amount ranging from 5% to 20% by weight, relative to the total weight of the composition.

14. The foundation composition according to claim 13, wherein the hydrophobic coated pigments are present in an amount at least equal to 8% by weight, relative to the total weight of the composition.

15. The foundation composition according to claim 14, wherein the hydrophobic coated pigments are present in an amount ranging from 8% to 15% by weight, relative to the total weight of the composition.

16. The foundation composition according to claim 1, wherein the at least one oil is present in an amount ranging from 20% to 45% by weight, relative to the total weight of the composition.

17. The foundation composition according to claim 16, wherein the at least one oil is present in an amount ranging from 30% to 38% by weight, relative to the total weight of the composition.

18. The foundation composition according to claim 1, wherein the fatty phase further comprises at least one fatty substance chosen from waxes, gums, and pasty fatty substances.

19. The foundation composition according to claim 1, further comprising at least one fatty phase thickening agent.

20. The foundation composition according to claim 19, wherein the at least one fatty phase thickening agent is chosen from organomodified clays and hydrophobic pyrogenic silicas.

21. The foundation composition according to claim 19, wherein the at least one fatty phase thickening agent is present in an amount ranging from 0.1% to 5% by weight, relative to the total weight of the composition.

22. The foundation composition according to claim 21, wherein the at least one fatty phase thickening agent is present in an amount ranging from 0.4% to 3% by weight, relative to the total weight of the compostion.

23. The foundation composition according to claim 1, wherein the fatty phase is present in an amount ranging from 22% to 50% by weight, relative to the total weight of the composition.

24. The foundation composition according to claim 23, wherein the fatty phase is present in an amount ranging from 25% to 45% by weight, relative to the total weight of the composition.

25. The foundation composition according to claim 24, wherein the fatty phase is present in an amount ranging from 30% to 40% by weight, relative to the total weight of the composition.

26. The foundation composition according to claim 1, wherein the aqueous phase is present in an amount ranging from 30% to 75% by weight, relative to the total weight of the composition.

27. The foundation composition according to claim 26, wherein the aqueous phase is present in an amount ranging from 35% to 50% by weight, relative to the total weight of the composition.

28. The foundation composition according to claim 1, wherein the aqueous phase comprises at least one solvent chosen from primary alcohols, glycols, and glycol ethers.

29. The foundation composition according to claim 1, wherein the aqueous phase comprises at least one stabilizing agent.

30. The foundation composition according to claim 1, further comprising at least one filler.

31. The foundation composition according to claim 30, wherein the at least one filler is chosen from talc, mica, silica, kaolin, starch, boron nitride, calcium carbonate, magnesium carbonate, magnesium hydrocarbonate, microcrystalline cellulose, polyethylene powders, polyesters, polyamides, polytetrafluoroethylene, and silicone powders.

32. The foundation composition according to claim 30, wherein the at least one filler is present in an amount ranging from 0.1% to 15% by weight, relative to the total weight of the composition.

33. The foundation composition according to claim 32, wherein the at least one filler is present in an amount ranging from 0.1% to 10% by weight, relative to the total weight of the composition.

34. The foundation composition according to claim 1, further comprising at least one additive chosen from gelling agents; hydrophilic and lipophilic thickening agents; moisturizing agents; emollients; hydrophilic and lipophilic active agents; anti-free radical agents; sequestrants; antioxidants; preservatives; basifying and acidifying agents; perfumes; film-forming agents; and soluble colorants.

35. The foundation composition according to claim 1, wherein the composition has a viscosity, measured at 25° C., at a shear rate of 200 revolutions per minute, ranging from 0.5 to 3.2 Pa.s.

36. The foundation composition according to claim 35, wherein the composition has a viscosity, measured at 25° C., at a shear rate of 200 revolutions per minute, ranging from 0.6 to 1.5 Pa.s.

37. A process for non-therapeutic application of make-up to skin comprising applying to the skin a foundation composition in the form of a water-in-oil emulsion comprising:
a fatty phase;
an aqueous phase;
at least one silicone surfactant chosen from $C_8$-$C_{22}$ alkyl dimethicone copolyols;
at least 5% by weight, relative to the total weight of the composition, of hydrophobic coated pigments,
at least one oil,
and a polyglyceryl-4 isostearate in a quantity such that the weight ratio of the $C_8$-$C_{22}$ alkyl dimethicone copolyol to the polyglyceryl-4 isostearate is greater than or equal to 2:1, wherein said at least one oil is chosen from at least one of octamethylcyclotetrasiloxane, decamethylcyclopentasiloxane, hexadecamethyl-cyclohexasiloxane, heptamethylhexyltrisiloxane, heptamethyloctyltrisiloxane., polydimethylsiloxanes, phenylated silicone oils, polysiloxanes modified with at least one entity chosen from fatty acids, fatty alcohols, and polyoxyalkylenes, paraffin oils, liquid paraffin oils, soya bean oil, perhydrosqualene, sweet almond oil, calophyllum oil, palm oil, grapeseed oil, sesame oil, maize oil, arara oil, rapeseed oil, sunflower oil, cottonseed oil, apricot oil, castor oil, avocado oil, jojoba oil, olive oil, cereal germ oil; esters of lanolic acid, oleic acid, lauric acid, stearic acid; isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate, 2-octyldodecyl lactate, 2-diethylhexyl succinate, diisostearyl malate, glycerine triisostearate, diglycerine triisostearate; myristic acid, palmitic acid, stearic acid, behenic acid, oleic acid, linoleic acid, linolenic acid, isostearic acid; cetanol, stearyl alcohol, oleyl alcohol, linoleyl alcohol, linolenyl alcohol, isostearyl alcohol, and octyldodecanol.

38. A process for making a foundation composition, comprising including at least one silicone surfactant chosen from $C_8$-$C_{22}$ alkyl dimethicone copolyols in the composition in the form of a water-in-oil emulsion comprising at least 5% by weight, relative to the total weight of the composition, of hydrophobic coated pigments, at least one oil,
and a polyglyceryl-4 isostearate in a quantity such that the weight ratio of the $C_8$-$C_{22}$ alkyl dimethicone copolyol to the polyglyceryl-4 isostearate is greater than or equal to 2:1;
wherein the composition has at least one of properties of being stable, homogeneous, and easily applied to the skin, and wherein said at least one oil is chosen from at least one of octamethylcyclotetrasiloxane, decamethylcyclopentasiloxane, hexadecamethyl-cyclohexasiloxane, heptamethylhexyltrisiloxane, heptamethyloctyltrisiloxane, polydimethylsiloxanes, phenylated silicone oils, polysiloxanes modified with at least one entity chosen from fatty acids, fatty alcohols, and polyoxyalkylenes, paraffin oils, liquid paraffin oils, soya bean oil, perhydrosqualene, sweet almond oil, calophyllum oil, palm oil, grapeseed oil, sesame oil, maize oil, arara oil, rapeseed oil, sunflower oil, cottonseed oil, apricot oil, castor oil, avocado oil, jojoba oil, olive oil, cereal germ oil; esters of lanolic acid, oleic acid, lauric acid, stearic acid; isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate, 2-octyldodecyl lactate, 2-diethylhexyl succinate, diisostearyl malate, glycerine triisostearate, diglycerine triisostearate; myristic acid, palmitic acid, stearic acid, behenic acid, oleic acid, linoleic acid, linolenic acid, isostearic acid; cetanol, stearyl alcohol, oleyl alcohol, linoleyl alcohol, linolenyl alcohol, isostearyl alcohol, and octyldodecanol.

39. A process for obtaining a homogeneous application of make-up to skin, comprising including at least one silicone surfactant chosen from $C_8$-$C_{22}$ alkyl dimethicone copolyols in the composition in the form of a water-in-oil emulsion comprising at least 5% by weight, relative to the total weight of the composition, of hydrophobic coated pigments, at least one oil, and a polyglyceryl-4 isostearate in a quantity such that the weight ratio of the $C_8$-$C_{22}$ alkyl dimethicone copolyol to the polyglyceryl-4 isostearate is greater than or equal to 2:1;
wherein the composition is homogeneous, wherein said at least one oil is chosen from at least one of octamethylcyclotetrasiloxane, decamethylcyclopentasiloxane, hexadecamethyl-cyclohexasiloxane, heptamethylhexyltrisiloxane, heptamethyloctyltrisiloxane, polydimethylsiloxanes, phenylated silicone oils, polysiloxanes modified with at least one entity chosen from fatty acids, fatty alcohols, and polyoxyalkylenes, paraffin oils, liquid paraffin oils, soya bean oil, perhydrosqualene, sweet almond oil, calophyllum oil, palm oil, grapeseed oil, sesame oil, maize oil, arara oil, rapeseed oil, sunflower oil, cottonseed oil, apricot oil, castor oil, avocado oil, jojoba oil, olive oil, cereal germ oil; esters of lanolic acid, oleic acid, lauric acid, stearic acid; isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate, 2-octyldodecyl lactate, 2diethylhexyl succinate, diisostearyl malate, glycerine triisostearate, diglycerine triisostearate; myristic acid, palmitic acid, stearic acid, behenic acid, oleic acid, linoleic acid, linolenic acid, isostearic acid; cetanol, stearyl alcohol, oleyl alcohol, linoleyl alcohol, linolenyl alcohol, isostearyl alcohol, and octyldodecanol.

40. A foundation composition in the form of an water-in-oil emulsion, comprising:
   at least one silicone surfactant chosen from $C_8$-$C_{22}$ alkyl dimethicone copolyols;
   at least 5% by weight, relative to the total weight of the composition, of hydrophobic coated pigments,
   at least one oil, and
   a polyglyceryl-4 isostearate in a quantity such that the weight ratio of the $C_8$-$C_{22}$ alkyl dimethicone copolyol to the polyglyceryl-4 isostearate is greater than or equal to 2:1;

wherein the composition has at least one of properties of being stable, homogeneous, and easily applied to the skin, wherein said at least one oil is chosen from at least one of octamethylcyclotetrasiloxane, decamethylcyclopentasiloxane, hexadecamethyl-cyclohexasiloxane, heptamethylhexyltrisiloxane, heptamethyloctyltrisiloxane., polydimethylsiloxanes, phenylated silicone oils, polysiloxanes modified with at least one entity chosen from fatty acids, fatty alcohols, and polyoxyalkylenes, paraffin oils, liquid paraffin oils, soya bean oil, perhydrosqualene, sweet almond oil, calophyllum oil, palm oil, grapeseed oil, sesame oil, maize oil, arara oil, rapeseed oil, sunflower oil, cottonseed oil, apricot oil, castor oil, avocado oil, jojoba oil, olive oil, cereal germ oil; esters of lanolic acid, oleic acid, lauric acid, stearic acid; isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate, 2-octyldodecyl lactate, 2-diethylhexyl succinate, diisostearyl malate, glycerine triisostearate, diglycerine triisostearate; myristic acid, palmitic acid, stearic acid, behenic acid, oleic acid, linoleic acid, linolenic acid, isostearic acid; cetanol, stearyl alcohol, oleyl alcohol, linoleyl alcohol, linolenyl alcohol, isostearyl alcohol, and octyldodecanol.

* * * * *